US008636805B2

(12) United States Patent
Jansen et al.

(10) Patent No.: US 8,636,805 B2
(45) Date of Patent: Jan. 28, 2014

(54) ARTIFICIAL INTERVERTEBRAL DISC PLACEMENT SYSTEM

(75) Inventors: Neville Jansen, Waterkloof (ZA); Malan de Villiers, Wapadrand (ZA)

(73) Assignee: SpinalMotion, Inc., Mountain View, CA (US)

( * ) Notice: Subject to any disclaimer, the term of this patent is extended or adjusted under 35 U.S.C. 154(b) by 0 days.

(21) Appl. No.: 13/476,845

(22) Filed: May 21, 2012

(65) Prior Publication Data

US 2012/0232662 A1   Sep. 13, 2012

Related U.S. Application Data

(62) Division of application No. 12/504,033, filed on Jul. 16, 2009, now Pat. No. 8,206,449.

(60) Provisional application No. 61/018,441, filed on Jul. 17, 2008.

(51) Int. Cl.
*A61F 2/44* (2006.01)
*A61B 17/70* (2006.01)
*A61B 17/88* (2006.01)

(52) U.S. Cl.
USPC ........................................ 623/17.16; 606/279

(58) Field of Classification Search
USPC ....... 606/246, 279, 90, 105, 86 A; 623/17.11, 623/17.1, 17.165
See application file for complete search history.

(56) References Cited

U.S. PATENT DOCUMENTS

| 3,486,505 A | 12/1969 | Morrison |
| 3,867,728 A | 2/1975 | Stubstad et al. |
| 4,309,777 A | 1/1982 | Patil |
| 4,531,917 A | 7/1985 | Linkow et al. |
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buttner-Janz et al. |
| 4,759,769 A | 7/1988 | Hedman et al. |

(Continued)

FOREIGN PATENT DOCUMENTS

| DE | 3023353 A1 | 4/1981 |
| EP | 0333990 A2 | 9/1989 |

(Continued)

OTHER PUBLICATIONS

Buttner-Janz, The Development of.the Artificial Disc. Introduction, pp. 1-18, Library of Congress Catalogue No. 92-75582, ISBN 0-9635430-0-8 (1989).

(Continued)

*Primary Examiner* — Pedro Philogene
*Assistant Examiner* — David Comstock
(74) *Attorney, Agent, or Firm* — Wilson, Sonsini, Goodrich & Rosati

(57) ABSTRACT

An intervertebral disc placement system includes a multi part intervertebral disc, such as a mobile core disc, and an associated placement instrument. The placement instrument holds the disc securely with the disc endplates angled for ease of placement of the disc into an intervertebral disc space and quickly releases the implant within the disc space. The disc includes upper and lower plates having notches in inner surfaces for engagement of the placement instrument. The placement instrument has a rotatable key configured to fit into the first and second notches to grasp the disc from the interior and eliminate the need for an external grasping mechanism which could interfere with disc placement.

9 Claims, 5 Drawing Sheets

(56) References Cited

U.S. PATENT DOCUMENTS

| | | |
|---|---|---|
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,314,477 A | 5/1994 | Marnay |
| 5,320,644 A | 6/1994 | Baumgartner |
| 5,370,697 A | 12/1994 | Baumgartner |
| 5,394,457 A | 2/1995 | Leibinger et al. |
| 5,401,269 A | 3/1995 | Buttner-Janz et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Buttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schar et al. |
| 6,193,757 B1 | 2/2001 | Foley et al. |
| 6,224,595 B1 | 5/2001 | Michelson |
| 6,224,607 B1 | 5/2001 | Michelson |
| 6,231,609 B1 | 5/2001 | Mehdizadeh |
| 6,235,030 B1 | 5/2001 | Zuckerman et al. |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba Rao et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Karus |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer, II et al. |
| 6,666,866 B2 | 12/2003 | Mertz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,755,841 B2 | 6/2004 | Fraser et al. |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthan |
| 6,821,298 B1 | 11/2004 | Jackson |
| 6,827,740 B1 | 12/2004 | Michelson |
| 6,846,328 B2 | 1/2005 | Cauthen |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,989,011 B2 | 1/2006 | Paul et al. |
| 6,994,727 B2 | 2/2006 | Khandkar et al. |
| 7,011,684 B2 | 3/2006 | Eckman |

(56) References Cited

U.S. PATENT DOCUMENTS

| | | |
|---|---|---|
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,583 B1 | 12/2007 | Schar et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | de Villiers et al. |
| 7,452,380 B2 | 11/2008 | Zubok et al. |
| 7,491,241 B2 | 2/2009 | Errico et al. |
| 7,494,508 B2 | 2/2009 | Zeegers |
| 7,531,001 B2 | 5/2009 | de Villiers et al. |
| 8,206,449 B2 | 6/2012 | Jansen et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree |
| 2003/0083747 A1 | 5/2003 | Winterbottom et al. |
| 2003/0100951 A1 | 5/2003 | Serhan et al. |
| 2003/0125739 A1 | 7/2003 | Bagga et al. |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2004/0002761 A1 | 1/2004 | Rogers et al. |
| 2004/0024407 A1 | 2/2004 | Ralph |
| 2004/0024410 A1 | 2/2004 | Olson et al. |
| 2004/0030387 A1 | 2/2004 | Landry et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Feree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | de Villiers et al. |
| 2005/0021146 A1 | 1/2005 | de Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0192586 A1 | 9/2005 | Zuckerman et al. |
| 2005/0192670 A1 | 9/2005 | Zubok et al. |
| 2005/0197706 A1 | 9/2005 | Hovorka et al. |
| 2005/0216081 A1 | 9/2005 | Taylor |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |
| 2006/0020342 A1 | 1/2006 | Ferree et al. |
| 2006/0025862 A1 | 2/2006 | de Villiers et al. |
| 2006/0029186 A1 | 2/2006 | de Villiers et al. |
| 2006/0030857 A1 | 2/2006 | de Villiers et al. |
| 2006/0030862 A1 | 2/2006 | de Villiers et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Feree |
| 2006/0069439 A1 | 3/2006 | Zucherman et al. |
| 2006/0142858 A1 | 6/2006 | Colleran |
| 2006/0142862 A1 | 6/2006 | Diaz et al. |
| 2006/0155378 A1 | 7/2006 | Eckman |
| 2006/0167549 A1 | 7/2006 | Mathys et al. |
| 2006/0178744 A1 | 8/2006 | de Villiers et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |

(56) References Cited

U.S. PATENT DOCUMENTS

| | | |
|---|---|---|
| 2006/0259144 A1 | 11/2006 | Trieu |
| 2006/0259146 A1 | 11/2006 | Navarro et al. |
| 2006/0265068 A1 | 11/2006 | Schwab |
| 2006/0293752 A1 | 12/2006 | Moumene et al. |
| 2006/0293754 A1 | 12/2006 | de Villiers et al. |
| 2007/0010826 A1 | 1/2007 | Rhoda et al. |
| 2007/0021837 A1 | 1/2007 | Ashman et al. |
| 2007/0032875 A1 | 2/2007 | Blacklock et al. |
| 2007/0061011 A1 | 3/2007 | de Villiers et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168036 A1 | 7/2007 | Ainsworth et al. |
| 2007/0179615 A1 | 8/2007 | Heinz et al. |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270970 A1 | 11/2007 | Trieu |
| 2007/0282449 A1 | 12/2007 | de Villiers et al. |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | de Villiers et al. |
| 2008/0051901 A1 | 2/2008 | de Villiers et al. |
| 2008/0065219 A1 | 3/2008 | Dye |
| 2008/0125864 A1 | 5/2008 | de Villiers et al. |
| 2008/0133011 A1 | 6/2008 | de Villiers et al. |
| 2008/0154301 A1 | 6/2008 | de Villiers et al. |
| 2008/0154382 A1 | 6/2008 | de Villiers et al. |
| 2008/0215155 A1 | 9/2008 | de Villiers et al. |
| 2008/0221696 A1 | 9/2008 | de Villiers et al. |
| 2008/0228274 A1 | 9/2008 | de Villiers et al. |
| 2008/0228277 A1 | 9/2008 | de Villiers et al. |
| 2008/0294259 A1 | 11/2008 | de Villiers et al. |
| 2009/0043391 A1 | 2/2009 | de Villiers et al. |
| 2009/0048674 A1 | 2/2009 | Zubok et al. |
| 2009/0048677 A1 | 2/2009 | McLeod et al. |
| 2009/0076614 A1 | 3/2009 | Arramon |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0222101 A1 | 9/2009 | de Villiers et al. |
| 2009/0276051 A1 | 11/2009 | Arramon et al. |
| 2010/0004746 A1 | 1/2010 | Arramon |
| 2010/0016973 A1 | 1/2010 | de Villiers et al. |

FOREIGN PATENT DOCUMENTS

| | | |
|---|---|---|
| EP | 0333990 A3 | 5/1990 |
| EP | 0560140 A1 | 9/1993 |
| EP | 0560141 A1 | 9/1993 |
| EP | 0591712 A1 | 4/1994 |
| EP | 0820740 A1 | 1/1998 |
| EP | 1142544 A1 | 10/2001 |
| EP | 1153582 A2 | 11/2001 |
| EP | 1153582 A3 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1405615 A1 | 4/2004 |
| EP | 1417940 A1 | 5/2004 |
| EP | 1570813 A1 | 9/2005 |
| FR | 2803741 A1 | 7/2001 |
| JP | 61122859 A | 6/1986 |
| JP | 63164948 A | 7/1988 |
| JP | 01136655 | 5/1989 |
| JP | 06007391 | 1/1994 |
| JP | 2002521090 | 7/2002 |
| JP | 2003508119 | 3/2003 |
| WO | WO 99/20209 A1 | 4/1999 |
| WO | WO 99/30651 A1 | 6/1999 |
| WO | WO 00/04851 A1 | 2/2000 |
| WO | WO 00/35384 A1 | 6/2000 |
| WO | WO 00/42954 A2 | 7/2000 |
| WO | WO 00/42954 A3 | 11/2000 |
| WO | WO 01/01893 A1 | 1/2001 |
| WO | WO 01/15637 A1 | 3/2001 |
| WO | WO 01/68003 A1 | 9/2001 |
| WO | WO 02/11650 A2 | 2/2002 |
| WO | WO 02/11650 A3 | 9/2003 |
| WO | WO 2004/000170 A1 | 12/2003 |
| WO | WO 2004/000171 A1 | 12/2003 |
| WO | WO 2004/026187 A1 | 4/2004 |
| WO | WO 2004/041131 A2 | 5/2004 |
| WO | WO 2004/054477 A1 | 7/2004 |
| WO | WO 2005/004756 A2 | 1/2005 |
| WO | WO 2005/004756 A3 | 5/2005 |
| WO | WO 2005/053580 A1 | 6/2005 |
| WO | WO 2005/072662 A1 | 8/2005 |
| WO | WO 2005/112834 A2 | 12/2005 |
| WO | WO 2005/112834 A3 | 5/2006 |
| WO | WO 2006/119092 A2 | 11/2006 |
| WO | WO 2006/119092 A3 | 12/2006 |
| WO | WO 2007/121320 A2 | 10/2007 |
| WO | WO 2007/121320 A3 | 6/2008 |
| ZA | 2003/9312 | 11/2003 |

OTHER PUBLICATIONS

Hellier, et al., Wear Studies for Development of an Intervertebral Disc Prosthesis. Spine, vol. 17 No. 6 Supplement pp. 86-96 (1992).

International search report and written opinion dated Feb. 24, 2010 for PCT/US2009/050572.

Lee, et al. Impact Response of the Intervertebral Disc in a Finite-Element Model. Spine. 2000; 25(19):2431-2439.

Lehuec, et al. Shock Absorption in Lumber Disc Prosthesis. Journal of Spinal Disorders & Techniques. 2003; 16(4):346-351.

Office action dated Dec. 21, 2011 for U.S. Appl. No. 12/504,033.

European search report and opinion dated Jul. 1, 2013 for EP Application No. 09798670.7.

ARTIFICIAL INTERVERTEBRAL DISC PLACEMENT SYSTEM

CROSS-REFERENCES TO RELATED APPLICATIONS

This application is a divisional of U.S. application Ser. No. 12/504,033, filed Jul. 16, 2009, which claims priority to U.S. Provisional Application No. 61/018,441, filed Jul. 17, 2008, entitled "ARTIFICIAL INTERVERTEBRAL DISC PLACEMENT SYSTEM" the full disclosures of which are incorporated herein by reference.

BACKGROUND OF THE INVENTION

The present invention relates to medical devices and methods. More specifically, the present invention relates to intervertebral disc prostheses.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without fusion of the two vertebrae adjacent to the disc. Fusion of the two vertebrae is achieved by inserting bone graft material between the two vertebrae such that the two vertebrae and the graft material grow together. Oftentimes, pins, rods, screws, cages and/or the like are inserted between the vertebrae to act as support structures to hold the vertebrae and graft material in place while they permanently fuse together. Although fusion often treats the back pain, it reduces the patient's ability to move, because the back cannot bend or twist at the fused area. In addition, fusion increases stresses at adjacent levels of the spine, potentially accelerating degeneration of the adjacent discs.

In an attempt to treat disc related pain without fusion, an alternative approach has been developed, in which a movable, implantable, artificial intervertebral disc (or "disc prosthesis") is inserted between two vertebrae. A number of different artificial intervertebral discs are currently being developed. For example, U.S. Patent Application Publication Nos. 2005-0021146, 2005-0021145, and 2006-0025862, which are hereby incorporated by reference in their entirety, describe artificial intervertebral discs. This type of intervertebral disc has upper and lower plates positioned against the vertebrae and a mobile core positioned between the two plates to allow articulation, translation and rotational motion between the vertebrae.

Another example of an intervertebral disc prostheses having a movable core is the CHARITE artificial disc (provided by DePuy Spine, Inc.) and described in U.S. Pat. No. 5,401,269. Other examples of intervertebral disc prostheses include MOBIDISC (provided by LDR Medical), the BRYAN Cervical Disc (provided by Medtronic Sofamor Danek, Inc.), and the PRODISC (from Synthes Stratec, Inc.) and described in U.S. Pat. No. 6,936,071. Some of these intervertebral discs are mobile core discs while others have a ball and socket type two piece design. Although existing disc prostheses provide advantages over traditional treatment methods, improvements are ongoing.

These known artificial intervertebral discs generally include upper and lower plates which locate against and engage the adjacent vertebral bodies, and a core for providing motion between the plates. The core may be movable or fixed, metallic, ceramic or polymer and generally has at least one convex outer articulation surface which mates with a concave articulation recess on one of the plates in a fixed core device. In a movable core device two sets of articulation surfaces are provided. In order to implant these intervertebral discs, the natural disc is removed and the vertebrae are distracted or forced apart in order to fit the artificial disc in place. The plates may be inserted individually or together and with or without a core. It is desirable to reduce the duration of the artificial disc procedure by implanting the disc in an assembled configuration. However, when holding the disc for implantation it is desirable to prevent contact of the placement tool with the bone integration surface of the disc to avoid damage to any bone integration structures or coatings thereon.

Currently available artificial intervertebral discs are held and delivered with a variety of different instruments and techniques. It would be desirable to provide a disc system with a simple placement instrument which easily and securely grasps the implant for insertion.

In addition, it would be desirable to hold the disc in the implantation instrument in an articulated or angled insertion configuration to prevent the need for over distraction of the disc space.

Therefore, a need exists for an improved artificial intervertebral disc placement system which securely and easily holds the articulating plates of the disc in a fixed arrangement suitable for placement of the disc.

BRIEF SUMMARY OF THE INVENTION

According to the invention there is provided an artificial disc placement system including a placement instrument with a quick and easy assembly mechanism and quick deployment.

In accordance with one aspect of the invention, an intervertebral disc placement system includes an artificial disc and a placement instrument. The artificial disc comprises an upper plate having an upper vertebra contacting surface and a lower surface having a bearing surface thereon; a lower plate having a lower vertebra contacting surface and an upper surface having a bearing surface thereon, wherein the upper and lower plates are configured to articulate with respect to one another; and a first notch in the lower surface of the upper plate and a second notch in the upper surface of the lower plate, wherein the first and second notches are aligned with one another. The placement instrument includes a handle and a rotatable key, wherein the key is configured to fit into the first and second notches.

In accordance with another embodiment of the invention, an intervertebral disc placement system includes an upper plate having an upper vertebra contacting surface and a lower surface having a bearing surface thereon; a lower plate having a lower vertebra contacting surface and an upper surface arranged to articulate with respect to the bearing surface of the upper plate; a first notch in the lower surface of the upper plate and a second notch in the upper surface of the lower plate, wherein the first and second notches are aligned with one another and face one another; and a placement instrument. The placement instrument has a handle and at least one movable key and the at least one key is configured to move into the first and second notches and retract toward the handle to secure the upper and lower plates to the placement instrument.

In accordance with a further embodiment of the invention, an intervertebral disc placement system includes an artificial disc and a placement instrument. The artificial disc comprises an upper plate having an upper vertebra contacting surface, a lower surface having an articulating surface thereon, anterior, posterior and two lateral edges; and a lower plate having a lower vertebra contacting surface, an upper articulating surface arranged to articulate with respect to the upper plate, anterior, posterior and two lateral edges. The placement instrument includes a handle and a disc receiving portion configured to receive the upper and lower plates of the artificial disc in the placement instrument in a locked configuration where the upper surface of the upper plate and the lower surface of the lower plate are angled such that the upper surface of the upper plate and the lower surface of the lower plate are closer together at an end of the disc remote from the placement instrument.

In accordance with an additional embodiment of the invention, an method of inserting an artificial disc into a space between two adjacent vertebrae includes the steps of: positioning the artificial disc on a placement instrument with upper and lower vertebrae contacting surfaces of the artificial disc positioned at an angle with respect to one another such that the vertebrae contacting surfaces are closer together at an end of the disc remote from the placement instrument; inserting the artificial disc partway into the space under constraint to prevent endplates of the prosthesis from articulating; releasing the prosthesis from constraint; and inserting the unconstrained prosthesis farther into the space.

Other features of the invention are set forth in the appended claims.

DETAILED DESCRIPTION OF THE INVENTION

An intervertebral disc placement system according to the present invention includes a multi part disc and an associated placement instrument. The placement instrument holds the disc securely for placement into an intervertebral disc space and quickly releases the implant within the disc space.

Figure 1:
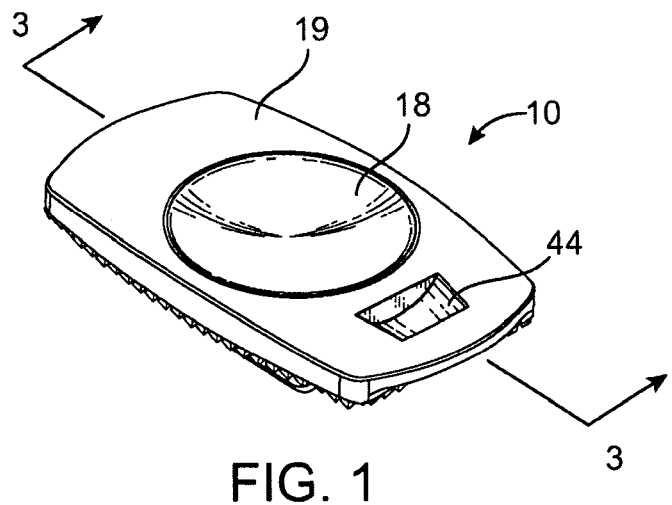
FIG. 1 is a bottom perspective view of a superior plate of an artificial disc.
Figure 2:
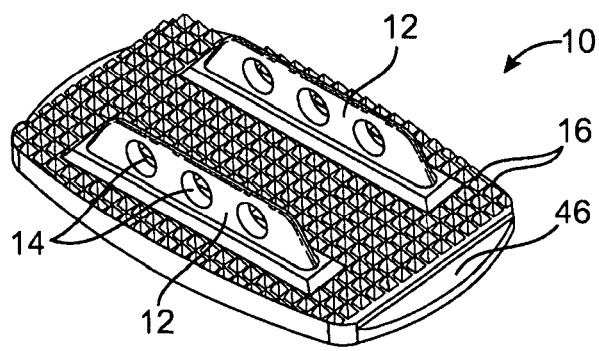
FIG. 2 is a top perspective view of the plate of FIG. 1.
Figure 3:
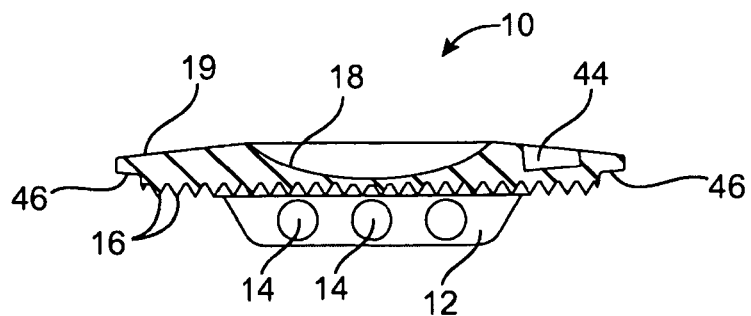
FIG. 3 is a side cross sectional view of the superior plate taken along line 3-3 of FIG. 1.
Figure 4:
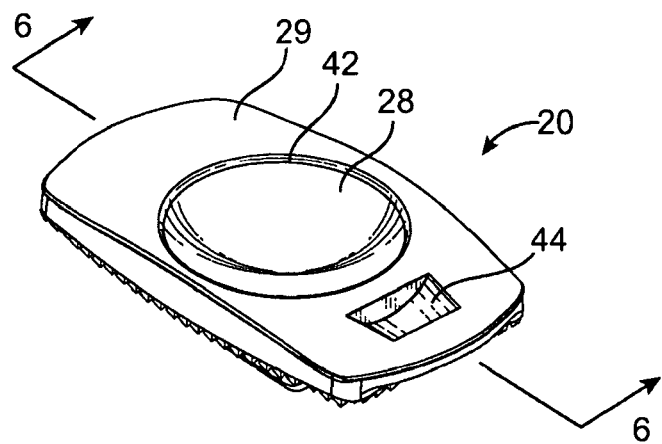
FIG. 4 is a top perspective view of an inferior plate of an artificial disc.
Figure 5:
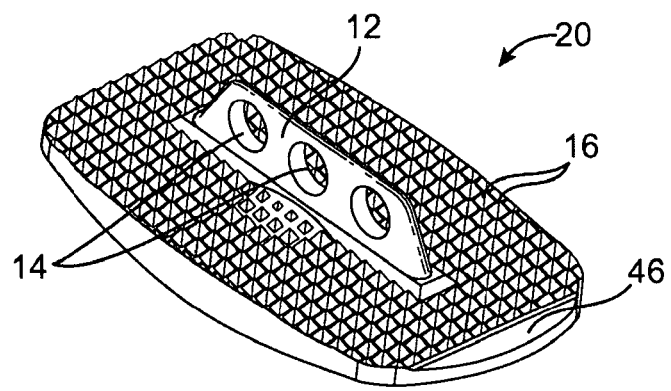
FIG. 5 is a bottom perspective view of the plate of FIG. 2.
Figure 6:
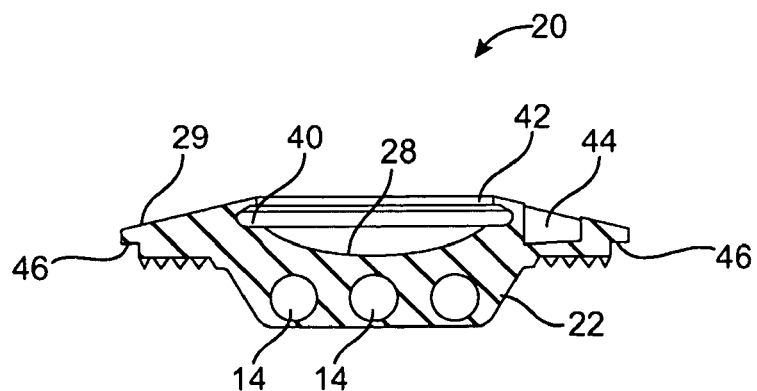
FIG. 6 is a side cross sectional view of the inferior plate taken along line 6-6 of FIG. 4.
Figure 7:
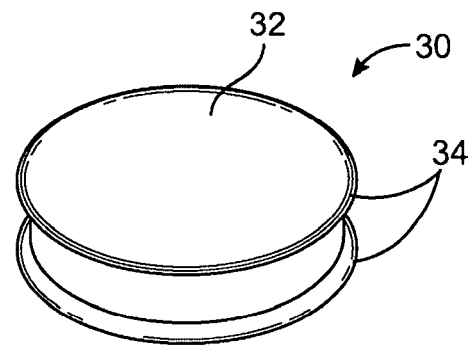
FIG. 7 is a perspective view of a core for use with the superior and inferior plates of FIGS. 1 and 4.

FIGS. 1-3 illustrate a superior or upper plate 10 of an intervertebral disc. FIGS. 4-6 illustrate a corresponding inferior or lower plate 20 and FIG. 7 illustrates a core 30 positionable between the plates to form a complete articulating intervertebral disc. The upper and lower plates 10, 20 include outer vertebral body contacting surfaces which are provided with attachment enhancing features to ensure bone integration. The attachment enhancing features shown include one or more fins and an array of serrations. In the embodiment shown the upper plate includes two fins 12 and the lower plate includes one fin 22. The fins 12, 22 can be an elongate fins pierced by one or more transverse holes 14 for bone ingrowth. The fins 12, 22 can have one or both ends formed at an angle, such as a 45 degree angle to aid in insertion of the fins into corresponding slots cut into the vertebral body. Particularly, the leading end of the fins 12, 22 should have an angled end surface.

The disc can be inserted laterally, from an anterior side, or from a posterior side. In the embodiment shown, the disc is designed for insertion laterally into an intervertebral space from either side. The lateral insertion of the disc is particularly useful in the lumbar spine where an anterior approach involves passing through the abdominal cavity and the posterior approach involve removal of a portion of the vertebra, such as the facets. Although the disc will be described herein as inserted laterally and is shown in a size appropriate for the lumbar spine, the system can be modified to accommodate other locations in the spine and other implantation approaches.

In the embodiment shown, two spaced apart superior fins 12 and a single central inferior fin 22 are provided on the upper and lower plates, respectively, extending in a lateral direction. Alternatively, one, two or more fins can be provided on either plate. In the example shown, the single fin is provided on one plate while the double fins are provided on the other plate to achieve a staggered arrangement particularly useful for multi-level disc implant procedures or in case an additional disc implant is required at a later time. The locations of the one and two fin plates can also be reversed so that the two fins are provided on the inferior plate. The orientation of the fin(s) 12, 22 can also be modified depending on the insertion direction for the intervertebral disc.

The fins 12, 22 are configured to be placed in slots in the vertebral bodies. The transverse holes 14 may be formed in any shape and may extend partially or all the way through the fins 12, 22. Preferably, the fins 12, 22 each have a height greater than a width and have a length greater than the height. The fin length is preferably greater than one half of a dimension of the plate in the corresponding direction.

The fins 12, 22 provide improved attachment to the bone and prevent rotation of the plates in the bone. In some embodiments, the fins 12, 22 may extend from the surface of the plates 10, 20 at an angle other than 90.degree. For example on one or more of the plates 10, 20 where multiple fins 12, 22 are attached to the surface the fins may be canted away from one another with the bases slightly closer together than their edges at an angle such as about 80-88 degrees. The fins 12, 22 may have any other suitable configuration including various numbers, angles, serrated edges, and curvatures, in various embodiments. In some embodiments, the fins 12, 22 may be omitted altogether.

The intervertebral body contacting surfaces of the plates 10, 20 also can include other geometries of bone integration structures including serrations, teeth, grooves, ridges, pins, barbs or the like. When the bone integration structures are ridges, teeth, barbs or similar structures, they may be angled to ease insertion and prevent migration. These bone integration structures can be used to precisely cut the bone during implantation to cause bleeding bone and encourage bone integration. Additionally, the outer surfaces of the plates 10, 12 may be provided with a rough microfinish formed by blasting with aluminum oxide microparticles or the like to improve bone integration. In some embodiments, the outer surface may also be titanium plasma sprayed or HA (hydroxylapatite) coated to further enhance attachment of the outer surface to vertebral bone.

The intervertebral body contacting surfaces shown include a plurality of serrations 16. The serrations 16 as shown are pyramid shaped serrations extending in mutually orthogonal directions, however, other shapes may also be used. The serrations have a height of about 0.5-1 mm and a width about equal to their height. With passage of time, firm connection between the plates 10, 20 and the vertebrae will be achieved as bone tissue grows over the serrated finish. Bone tissue growth will also take place about the fins 12, 22 and through the holes 14 therein, further enhancing the connection which is achieved.

Opposite the serrated vertebral body contacting surfaces of the plates 10, 20, the plates have concave bearing surfaces 18, 28. These concave bearing surfaces are shaped to accommodate and retain a mobile core. The particular shape and curvature of the bearing surfaces 18, 28 can vary to accommodate different shaped cores or different applications. Surrounding the bearing surfaces 18, 28 are angled surfaces 19, 29 which limit the articulation of the disc. The angle at which the surfaces 19, 29 are formed can be varied to form a disc with a selected maximum articulation. The maximum articulation can be different in each direction including the anterior, posterior and lateral directions. In one example, the disc is designed to allow angulations between the upper and lower plates of a maximum of .+−.12 degrees in the lateral direction, .+−.12 degrees in the anterior/posterior direction, and unlimited rotation.

The core 30, as shown in FIG. 7, can be formed as a circular disc shaped member with upper and lower bearing surfaces 32 which match the curvature of the concave bearing surfaces 18, 28 of the plates. The core 30 also has one or more annular rims 34 which cooperate with a retention feature 40 on at least one of the plates 10, 20 to retain the core between the plates when the intervertebral disc is implanted between the vertebrae of a patient. The core 30 is moveable with respect to both the upper and lower plates 10, 20 to allow articulation, translation and rotation of the upper and lower plates with respect to one another. The core bearing surfaces 32 and concave bearing surfaces 18, 28 of the plates have the same radius of curvature which may vary depending on the size of the intervertebral disc.

The retention feature 40 in the illustrated embodiment comprises a retention ring 42 on the lower plate 20, shown most clearly in FIG. 6. The retention ring 42 protrudes inwardly from an edge of the bearing surface 28. Although a circumferential core retaining feature is shown, other core retaining features may also be used including at least those shown in U.S. Patent Publication Nos. 2005/0251262, 2005/0021146, and 2005/0021145, which are incorporated herein by reference in their entirety.

Although the core 30 has been shown as circular in cross section with spherically shaped bearing surfaces 32, other shapes may be used including oval, elliptical, or kidney bean shaped. These non-circular shaped cores can be used to limit rotational motion between the upper and lower plates 10, 20. The bearing surfaces 18, 28, 32 of the plates and core are shown as spherical, however flat, cylindrical, tab and groove, stepped or other shaped bearing surfaces may also be used.

Although the core 30 and plates 10, 20 have been shown as solid members, the core and plates may be made in multiple parts and/or of multiple materials. The core can be made of low friction materials, such as titanium, titanium nitrides, other titanium based alloys, tantalum, nickel titanium alloys, stainless steel, cobalt chrome alloys, ceramics, or biologically compatible polymer materials including PEEK, UHMWPE, PLA or fiber reinforced polymers. High friction coating materials can also be used.

The present invention has been illustrated as a three piece articulating disc with a mobile core. The invention may also be embodied in a two piece or ball and socket type disc which can be held by a placement instrument in the same manner described below with respect to the three piece disc.

The intervertebral disc according to the present invention provides articulation in two directions as well as translation and rotation. The plates 10, 20 are provided with notches 44 at one lateral end of each plate for use in grasping the disc by a placement instrument 50 shown in FIG. 8. The placement instrument facilitates holding and manipulation of the disc for insertion or removal of the disc in an intervertebral disc space. The notches 44 allow the plates 10, 20 to be grasped and inserted simultaneously in a locked orientation with or without a core 30 there between. The lateral edges of the plates 10, 20 also include a stepped surface 46. On the end of the plates with the notches 22, the stepped surfaces 46 engage a corresponding abutment surface on the placement instrument to further secure the plates in the placement instrument.

The upper and lower plates 10, 20 may be formed from titanium, titanium nitrides, other titanium based alloys, tantalum, nickel titanium alloys, stainless steel, cobalt chrome alloys, ceramics, or biologically compatible polymer materials including PEEK, UHMWPE, PLA or fiber reinforced polymers. The bearing surfaces or recesses 18, 28 are concavely, spherically curved and can have a hard coating such as a titanium nitride finish. The plates 10, 20 may be treated with aluminum oxide blasting followed by a titanium plasma spray to improve bone integration. Other materials and coatings can also be used such as titanium coated with titanium nitride, aluminum oxide blasting, HA (hydroxylapatite) coating, micro HA coating, and/or bone integration promoting coatings. Any other suitable metals or combinations of metals may be used as well as ceramic or polymer materials, and combinations thereof to optimize imaging characteristics. Any suitable technique may be used to couple materials together, such as snap fitting, slip fitting, lamination, interference fitting, use of adhesives, welding and/or the like.

Figure 8:
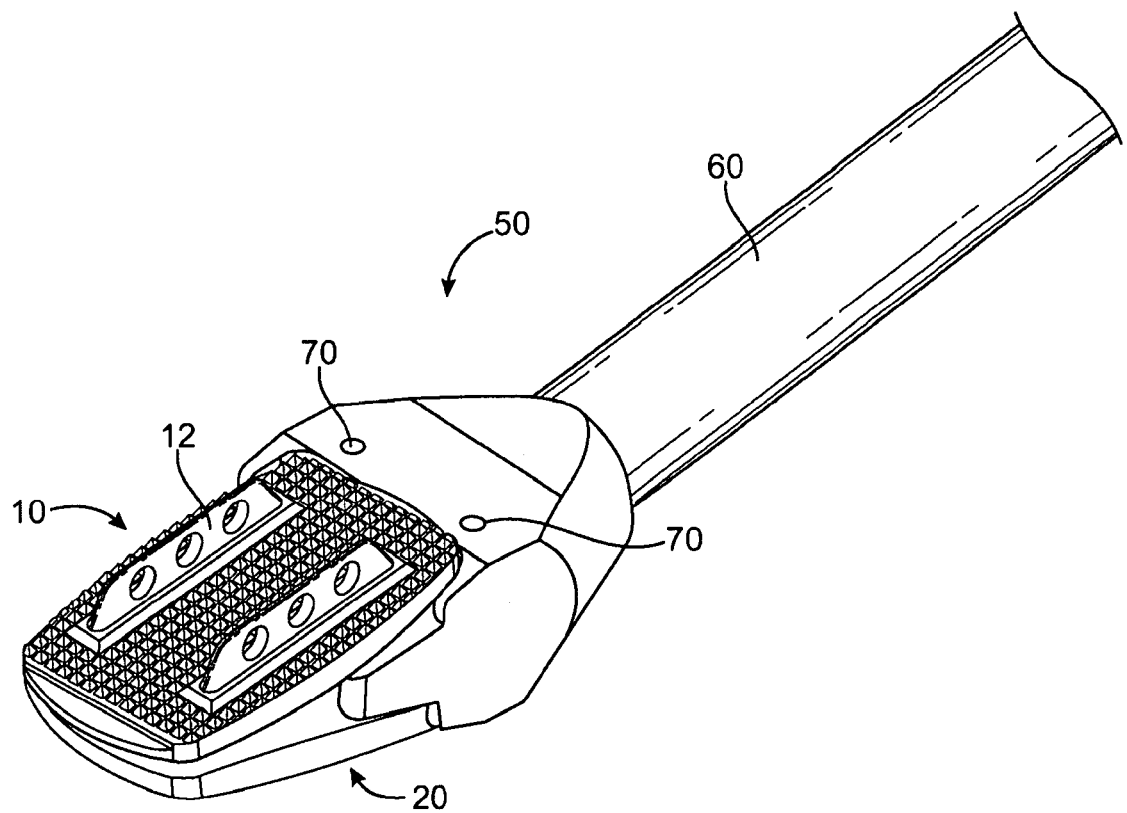
FIG. 8 is a perspective view of the assembled intervertebral disc held by an placement instrument.

FIG. 8 illustrates the plates 10, 20 secured in the placement instrument 50 and arranged with the upper plate at an angle with respect to the lower plate for placement of the disk. The angled placement orientation allows the plates 10, 20 to be inserted more easily into the intervertebral space with a narrow leading end formed by the angle of the plates. An angle between the upper vertebral body contacting surface of the upper plate 10 and the lower vertebral body contacting surface of the lower plate is at least 5 degrees. Preferably, the angle is about 15-30 degrees, and more preferably about 25 degrees.

Figure 9:
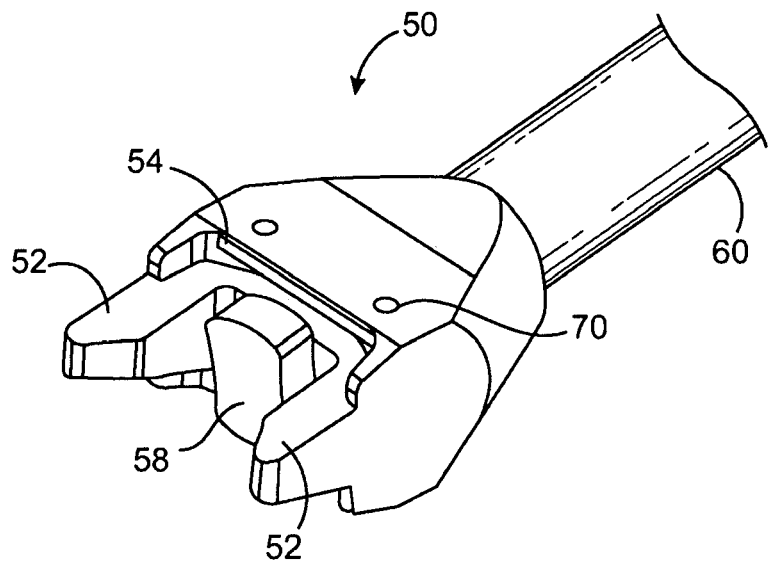
FIG. 9 is a perspective view of the placement instrument of FIG. 8.
Figure 10:
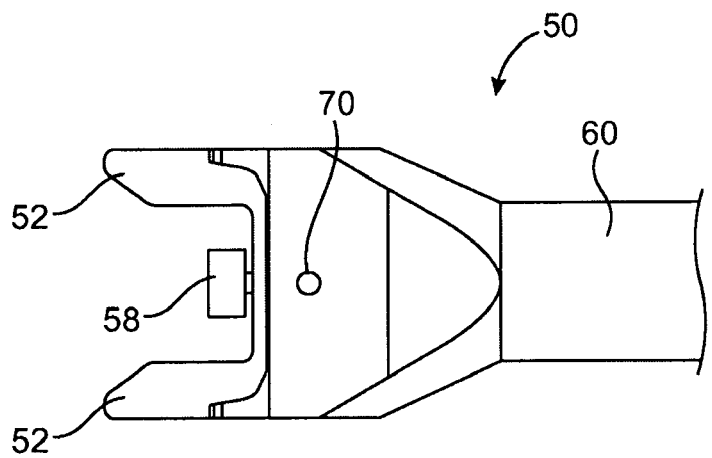
FIG. 10 is a top view of the placement instrument of FIG. 9.

FIG. 9 illustrates the disc holding end of the placement instrument 50 is mounted on a shaft 60. The instrument 50 includes a pair of arms 52 having flat surfaces on opposite top and bottom sides for supporting the plates interior surfaces. An abutment surface 54 overhangs a groove 56 which is configured to receive the protruding stepped surface at the ends of the 46 of the plates. A rotatable key 58 functions as a locking mechanism and is received in the notches 44 of the plates. The engagement of the rotatable key 58 in the notches 44 allows the plates 10, 20 to be made without any outwardly extending engagement features. This can provide an advantage of a lower profile over many of the know devices having exterior rims or grooves for engagement by a placement instrument. The key engagement system of the placement instrument also provides the advantage of a narrower placement profile than those placement instruments which grasp the side surfaces of a disc.

Figure 11:
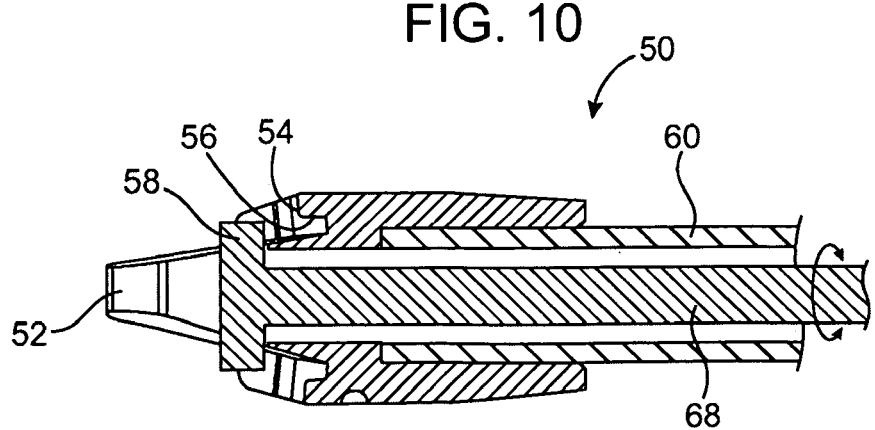
FIG. 11 is a side cross sectional view of the placement instrument taken along line 11-11 of FIG. 10.
Figure 12:
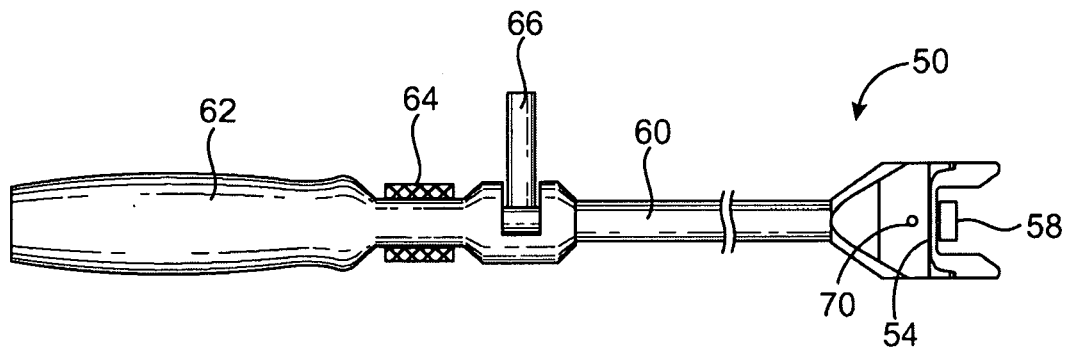
FIG. 12 is a top view of the placement instrument with a disc locking key in the unlocked position.
Figure 13:
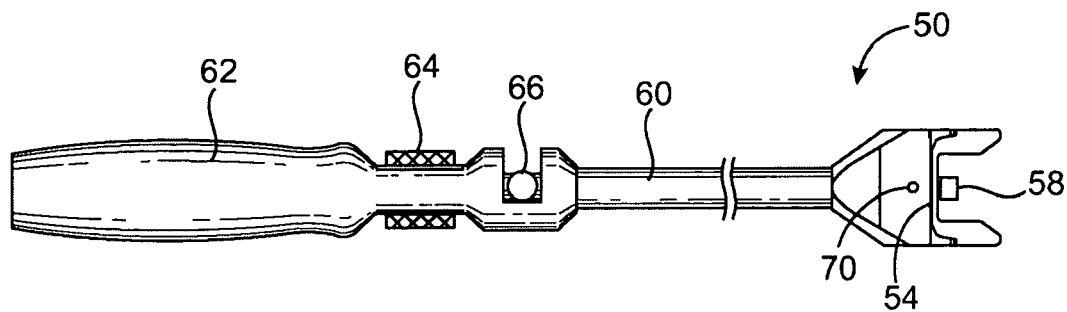
FIG. 13 is a top view of the placement instrument with the key in the locked position.

FIGS. 12 and 13 show the operation of the handle end of the placement instrument 50 which includes the handle 62, a rotatable knob 64, and a movable lever 66. The movable lever 66 is connected through a central shaft 68 of the handle (shown in FIG. 11) to the key 58 and functions as a key rotating mechanism to move the key from an unlocked position shown in FIG. 12 to a locked position shown in FIG. 13. The rotatable knob 64 functions as a retraction mechanism to retract the key 58 toward the handle 62 to secure the plates against the abutment surfaces 54. In operation, the plates 10, 20 are place in the disc holding end of the placement instrument with the notches 44 aligned over the key 58 and the key in the unlocked position of FIG. 12. The key 58 is then rotated 90 degrees by moving the lever 66 90 degrees causing the ends of the key to enter the notches 44. The plates 10, 20 are then pulled tight against the abutment surfaces 54 of the instrument by rotating the knob 64 to retract the key toward the handle. This pulls the key 58 against the side of the notches 44 to lock the plates tightly in place.

The disc holding end of the placement instrument 50 can be marked, such as by markers 70 which include either two dots or one dot indicating that the position for either a two fin or one fin plate. Other marking or indicia can also be used to identify the correct location and/or orientation of the plates, such as labeling (superior, inferior), color coding, or other insignia.

The artificial intervertebral disc is surgically implanted between adjacent spinal vertebrae in place of a damaged disc. Those skilled in the art will understand that the damaged disc is partially or totally removed according to known procedures and the adjacent vertebrae are forcibly separated from one another to provide the necessary space for insertion of the disc. The plates 10, 20 are slipped into place between the vertebrae with their fins 12, 22 entering slots cut in the opposing vertebral surfaces to receive them. The plates 10, 20 may be inserted simultaneously with or without the core 30. The disc may be inserted all the way to a final resting place with the placement instrument 50, or after partial insertion of the disc, the individual plates 10, 20 can be further advanced independently or together to a final position. The insertion of the disc partway into the intervertebral space while connected to the placement instrument and then the further insertion of the plates while they are free to move with respect to one another allows the disc to moved to a final position while it is free to take on the angulation or lordosis of the space. This reduces the problem of overdistraction of the disc space.

Once the disc has been partially or completely inserted, the placement instrument 50 is removed from the plates 10, 20 by simply rotating the lever 66 90 degrees back to the unlocked position of the key 58. Once the disc has been inserted, the vertebra move together to hold the assembled disc in place.

The vertebral contacting surfaces of the plates 10, 20 including the serrations 16 locate against the opposing vertebrae and, with passage of time, firm connection between the plates and the vertebrae will be achieved as bone tissue grows over the serrated finish. Bone tissue growth will also take place about the fins 12, 22 and through the holes 14 therein, further enhancing the connection which is achieved.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A method of inserting an artificial disc into a space between two adjacent vertebrae, the method comprising:
    positioning the artificial disc on a placement instrument with upper and lower vertebrae contacting surfaces of the artificial disc positioned at an angle with respect to one another such that the vertebrae contacting surfaces are closer together at an end of the disc remote from the placement instrument;
    rotating a key of the placement instrument to secure the artificial disc on the placement instrument by receiving ends of the key in notches on inner surfaces of the artificial disc;
    inserting the artificial disc partway into the space under constraint to prevent endplates of the prosthesis from articulating;
    releasing the prosthesis from constraint; and
    inserting the unconstrained prosthesis farther into the space.

2. The method of claim 1, wherein the upper and lower vertebrae contacting surfaces are angled at an angle of at least 15 degrees when the artificial disc is positioned on the placement instrument.

3. The method of claim 1, wherein a disc receiving portion of the placement instrument is configured to receive a lateral edge of the artificial disc and the steps of inserting the artificial disc include placement of the disc from a lateral aspect of a patient's spine.

4. The method of claim 1, wherein the upper plate is held by the placement instrument at an angle with respect to the lower plate for placement of the disk.

5. The method of claim 4, wherein the artificial disc is inserted into the space from a lateral aspect of a patient's spine.

6. A method of inserting an artificial disc into a space between two adjacent vertebrae, the method comprising:
    providing an artificial disc comprising:
        an upper plate having an upper vertebra contacting surface and a lower surface having a bearing surface thereon;

a lower plate having a lower vertebra contacting surface and an upper surface having a bearing surface thereon, wherein the upper and lower plates are configured to articulate with respect to one another; and a first notch in the lower surface of the upper plate and a second notch in the upper surface of the lower plate, wherein the first and second notches are aligned with one another; and positioning the upper and lower plates of the artificial disc on a placement instrument;

rotating a key of the placement instrument to secure the artificial disc on the placement instrument by receiving ends of the key in the first and second notches to constrain motion of both the upper and lower plates;

inserting the artificial disc into the space; and releasing the prosthesis from placement instrument.

7. The method of claim 6, wherein the placement instrument key has a locked position and an unlocked position, and wherein in the locked position the key is positioned with ends of the key in the first and second notches.

8. The method of claim 6, wherein the placement instrument includes first and second abutment surfaces configured to contact the upper surface of the upper plate and the lower surface of the lower plate.

9. The method of claim 6, wherein the placement instrument includes a disc holding end and a handle end, and wherein the key is an elongated member disposed at the holding end and rotatable by a key rotating mechanism at the handle end of the placement instrument.

* * * * *